(12) United States Patent
Santhanam

(10) Patent No.: US 11,654,108 B1
(45) Date of Patent: May 23, 2023

(54) SENNOSIDE MEDICATED CHEWS

(71) Applicant: MEDICATED CHEWS, LLC, East Hanover, NJ (US)

(72) Inventor: Karthikeyan Santhanam, Basking Ridge, NJ (US)

(73) Assignee: MEDICATED CHEWS, LLC, East Hanover, NJ (US)

( * ) Notice: Subject to any disclaimer, the term of this patent is extended or adjusted under 35 U.S.C. 154(b) by 0 days.

(21) Appl. No.: 17/734,794

(22) Filed: May 2, 2022

(51) Int. Cl.
A61K 9/00 (2006.01)
A61K 47/12 (2006.01)
A61K 47/36 (2006.01)
A61K 31/704 (2006.01)

(52) U.S. Cl.
CPC .......... *A61K 9/0056* (2013.01); *A61K 31/704* (2013.01); *A61K 47/12* (2013.01); *A61K 47/36* (2013.01)

(58) Field of Classification Search
CPC .... A61K 9/0056; A61K 31/704; A61K 47/12; A61K 47/36
USPC .......................................................... 514/33
See application file for complete search history.

(56) References Cited

U.S. PATENT DOCUMENTS

| 2005/0053676 A1* | 3/2005 | Schata ................ A61K 31/736 424/738 |
| 2005/0202084 A1* | 9/2005 | Adusumilli .......... A61K 9/0056 424/464 |
| 2017/0202833 A1 | 7/2017 | Iwamoto et al. |
| 2019/0364924 A1 | 12/2019 | Capdepon et al. |

FOREIGN PATENT DOCUMENTS

WO 2018236990 A1 12/2018

OTHER PUBLICATIONS

Ergül et al. (The Saudi Journal of Gastroenterology, vol. 20, No. 6, Nov. 2014, 356-359).*
Yu et al. (Huaxi Yaoxue Zazhi (2015), 30(4), 471-473) (abstract sent).*
Avrio Health L.P., "Senokot Dietary Supplement: Natural Senna Extract Laxative Gummies," Senokot®, Web page <https://senokot.com/laxatives/senokot-laxative-gummies/?gclid=EAIaIQobChMlqa09jcWR-AIVhP_jBx0PtAMDEAAYASAAEgJyGPD_BwE&gclsrc=aw.ds> Date Accessed Jun. 17, 2022.
European Pharmacopoeia 7.0, "2.9.40. Uniformity of Dosage Units," 2. Methods of Analysis:315-317 (2008).
Franz G., "The Senna Drug and Its Chemistry," Pharmacology, 47(suppl_1):2-6 (1993).
Geri-Care Pharmaceuticals Corp., "Health Star Natural Senna Extract: Laxative Dietary Supplement Product Label," Health Star®, Web page <http://www.gericarepharm.com/wp-content/uploads/2021/04/L9151-06-HST.pdf> Date Accessed Jun. 17, 2022.
Pharmvista Inc., "Orgalax Dietary Supplement: Natural Senna Extract Laxative Gummies Product Label," Orgalax®, Web page <https://orgalax.com/gummies.php> Date Accessed Jun. 17, 2022.
The United States Pharmacopeial Convention, "<905> Uniformity of Dosage Units," General Chapter, Stage 6 Harmonization:1-3 (2011).

* cited by examiner

*Primary Examiner* — Layla D Berry
(74) *Attorney, Agent, or Firm* — Medler Ferro Woodhouse & Mills PLLC

(57) ABSTRACT

The disclosure relates to a chewable medicated composition comprising sennosides as the active ingredient and at least one excipient, wherein the bitter taste of sennosides is masked and the composition is substantially free of sugar.

11 Claims, No Drawings

SENNOSIDE MEDICATED CHEWS

FIELD OF THE INVENTION

The disclosure relates to a chewable medicated composition comprising a sennoside as the active ingredient and at least one excipient, wherein the bitter taste of the sennoside is masked and the composition is substantially sugar free.

BACKGROUND

Chewable medicated compositions, also known as gummies, gummy bears, gum drops, jelly candy, gummi chews, medicated chews, chewable gels, chew gels, soft chews, gummy candy, gummies, jelly fruit candy, confectionery or jellies consist of gelling component(s) such as starch, gelatin, gluten, pectin and other binding agents of these kind. These dosage forms are intended to be chewed before being swallowed and may contain one or more active ingredients. Major ingredients of commercially available gummies include gelatin or pectin or agar (5-8%), water (15-20%), sucrose (28-50%), and corn syrup solids (40-55%). Typically, mass production involves use of gelatin base that's mixed and cooked in a cooker under steam and pressure, followed by mixing the cooked gelatin with flavors, colors, acids, fruit concentrates, active ingredients (if any). This is then followed by pumping the cooked gelatin stock into starch filled mold boards, also known as a mogul, to obtain desired shapes. The shaped candies are then cured to obtain the final product. The gummies also typically contain a large amount of sugar per serving or per unit or per gummy. The sugar not only helps in providing a better taste, but also contributes to the properties of the gummy.

Cassia angustifolia is an ayurvedic herb more popularly known as senna. The leaves and pods are administered in Ayurveda and Unani systems of medicine as infusion for their purgative properties, combined with carminatives and aromatics. Senna is available across 500 species, of which 26 species of genus Cassia have been reported to contain anthracene derivatives either in the free form or as glycosides. Of these, Cassia angustifolia (Indian senna) and Cassia acutifolia (Alexandrian senna) are official in different pharmacopoeias, because of laxative activity, and also because they are available in large quantities. The other species with known laxative activity are Cassia fistula, Cassia obovata, Cassia dentate, Cassia sofara, Cassia sieberiana, Cassia podocarpa, Cassia alata.

Senna is a stimulant laxative, used for the treatment of constipation and for the evacuation of the bowel prior to the diagnostic tests of gastrointestinal and colorectal area. Stimulant laxatives like senna work by irritating luminal sensory nerve endings, thereby stimulating colonic motility, reducing colonic water absorption and sodium reabsorption. Derivatives of diphenylmethane phenolphthalein (bisacodyl), the anthraquinones (sennosides, aloe, dantron, cascara), and castor oil are drugs in this category. Stimulant laxatives have been found to be more effective than stool-bulking agents for constipation in pregnancy. However, senna (approved by the USFDA under category C) was not found to be associated with a higher risk for congenital abnormalities or adverse birth outcomes.

The active principle of Senna was first isolated in 1941 by Stoll. The first two glycosides were identified and attributed to the anthraquinone family. These were found to be dimeric products of aloe emodin and/or rhein, which were named sennoside A and sennoside B (together sennosides). They both hydrolyze to give the aglycones sennidin A and B, and two molecules of glucose. Later work confirmed these findings and further demonstrated the presence of sennosides C and D. Small quantities of monomeric glycosides and free anthraquinones seem to be present as well. (See "The Senna drug and its Chemistry", Pharmacology 1993; 47 (suppl 1):2-6)

The β-O-linked glycosides (sennosides) are neither absorbed in the upper gut nor split by human digestive enzymes. They are converted by the bacteria of the large intestine into the active metabolite (rhein-9-anthrone). In contact with oxygen, rhein anthrone is oxidized into rhein and sennidins, which are found in the blood, mainly in the form of glucuronides and sulphates. After oral administration of sennosides, 3-6% of the metabolites are excreted in urine; some are excreted in bile. Most of the sennosides (90%) are excreted in feces as polymers (polyquinones) together with 2-6% of unchanged sennosides, sennidins, rheinanthrone and rhein.

Basic chemical structure of sennosides can be presented as below—

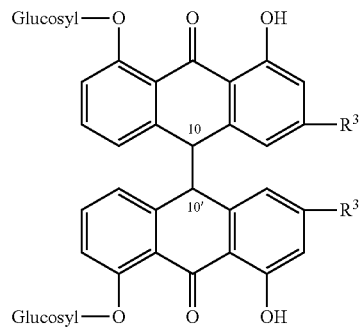

| R1 | R2 | 10-10' | Glycoside |
|---|---|---|---|
| COOH | COOH | Trans | Sennoside A |
| COOH | COOH | Meso | Sennoside B |
| CH2OH | COOH | Trans | Sennoside C |
| CH2OH | COOH | Meso | Sennoside D |

Senna is known for its bitter and pungent taste. Bitter taste in general is undesirable, and especially for oral chewable products. In order to overcome such undesirable taste, sugars or sweetening agents are added in large amounts. Apart from being detrimental in patients with diabetes, the high sugar content is also not advisable in obese patients. It must also be noted that products with such high sugar content also are responsible for tooth decay and dental issues. The high sugar content can also be a cause for concern in patients with gastric discomfort and those with celiac disease.

Because of its bitter taste, products containing senna are formulated with high sugar content, like Geri Care's senna gummies and Orgalax gummies, which are commercially available senna gummies, and both of which contain 4 to 6 gm of sugar per serving. Senokot gummies, considered the national brand, contain 6 gm of added sugar per serving. Each of these commercially available gummy preparations of senna have a serving size of 4 gummies, and contain 34.8 mg of senna leaf extract. The serving size of Senokot gummies and Orgalax gummies provides 40 calories.

US20170202833A1 in the name of Otsuka pharmaceuticals, attempted to mask the bitter taste of active ingredients (sennoside listed as one of them) with sugar alcohol and one or more hydrophilic polysaccharides. Sugar alcohol is a carbohydrate. Even though its impact on blood sugar is less than that of real sugar, it can raise blood sugar level when consumed regularly.

WO2018236990A1 in the name of Seattle Gummy Company, relates to gelatin gummy composition of laxatives. While this publication lists several active ingredients that can be incorporated into gelatin-containing gummies, gelatin is not preferred by vegetarian and vegan individuals.

The commercially available gummies are almost always obtained using gelatin and a process using a mogul. The starch thus used is a huge source of contamination and a major issue in maintaining clean facilities, thereby making it difficult to meet regulatory requirements on good manufacturing practices. Further, use of gelatin and starch requires the use of a consistent and high drying temperature, which makes it unsuitable for active ingredients and excipients that are thermolabile. The disadvantages of starch in manufacturing of gummies are further described in United States Patent publication 20190364924.

SUMMARY OF THE INVENTION

The present disclosure provides a chewable medicated composition comprising sennosides as the active ingredient, and at least one gelling agent. The chewable medicated compositions of the disclosure are stable, and substantially free of gelatin, sugar, and gluten. In one embodiment, the chewable medicated composition comprising sennoside has a content uniformity that meets the requirements of the USP<905>Uniformity of Dosage Units test or another analytical method for measuring content uniformity.

In another embodiment, the chewable medicated composition of the present disclosure containing sennosides is free of gelatin, and is substantially free of starch, sugar and gluten.

In another embodiment, the medicated chew comprises about 0.05% w/w to about 2.5% w/w sennoside, about 0.1% w/w to about 10% w/w of a gelling agent comprising from carrageenan, pectin or mixtures thereof, about 10% w/w to about 90% w/w of a sweetening agent, a buffer, wherein the pH of the composition is about 3 to about 6, wherein the medicated chew is substantially-free of gelatin, sugar, gluten. In yet another embodiment the medicated chew has a water activity of about 0.6 aw to about 0.85 aw.

The present disclosure also provides a method of manufacturing the chewable medicated composition comprising (a) melting a gel, (b) blending an active agent into the melted gel of (a), (c) blending an excipient into the blend of (b), (d) casting the blend of (c) into a mould, (e) drying the casted blend of (d), and optionally, (f) coating the dried, casted blend, wherein the process is free of use of gelatin and mogul.

In one embodiment of the present disclosure, the medicated chew comprises sennosides as a laxative agent, and the maximum daily dose of total sennosides does not exceed 50 mg, administered as 4 gummies.

In another embodiment, the medicated chew of the present disclosure comprises sennosides as the active ingredient used as a laxative for the treatment of constipation and for the evacuation of the bowel prior to diagnostic tests of the gastrointestinal and colorectal area.

In one embodiment, the chewable medicated composition contains sennosides as the active ingredient, and the composition meets all the FDA requirements for OTC monograph products for sennosides under 21 CFR part 334.

DETAILED DESCRIPTION OF THE INVENTION

The present disclosure provides for a medicated chew that overcomes disadvantages associated with agents such as gelatin and starch traditionally used in medicated chews. In some embodiments, the medicated chew improves patient compliance by providing a stable composition comprising a sennoside which is substantially free of gelatin, sugar, and gluten. The present disclosure also provides a medicated chew composition comprising sennosides having an acceptable content uniformity, and a small serving size.

The present disclosure provides sugar-free, gelatin-free gummy compositions comprising a sennoside, and which may be orally self-administered, are pleasant tasting and are free of drawbacks associated with many pharmaceutical preparations.

Certain segments of the population have difficulty ingesting and swallowing solid oral dosage forms such as tablets and capsules. As many as a quarter of the total population has this difficulty, also known as dysphagia. Often, this leads to non-compliance with the recommended medical therapy with the solid dosage forms, thereby resulting in rendering the therapy ineffective. Further, solid dosage forms are not recommended for children or elderly due to increased risk of choking. Thus, the present disclosure provides for a medicated chew that avoids the problems associated with solid dosage forms. As used herein, the term "medicated chew," "medicated chew compositions", and "chewable medicated composition" are interchangeable and refer to medicated gummies (e.g., gummy bears), gum drops, jelly candy, gummi chews, chewable gels, chew gels, soft chews, gummy candy, gummies, jelly fruit candy, confectionery or jellies, and other single-dose preparations which contain an active agent and a base (e.g., a gelling agent), wherein the medicated chew should be chewed in the buccal environment for a certain period of time before swallowing (i.e., ingesting).

The chewable medicated compositions of the present disclosure containing sennosides can be useful in pediatric and geriatric subjects who have anxiety over swallowing pills, and in subjects suffering from dysphagia. In some embodiments, the convenience of having the chewable medicated compositions described herein can also help improve compliance. Further, since the chewable medicated composition described herein is substantially free of gelatin, it is suitable to be used by vegetarian and vegan individuals who avoid animal origin products. The chewable medicated compositions of the present disclosure are also substantially free of sugar, thereby making them suitable and advantageous in subjects with diabetes, those wanting to keep sugar consumption low, and in children and/or individuals that may have dental issues such as cavities.

In some embodiments, the medicated chew described herein comprises about 2 mg to about 35 mg sennoside, about 4 mg to about 10 mg sennoside, or about 4 mg to about 6 mg sennoside. In some embodiments, the medicated chew comprises a minimum of about 4.3 mg sennoside. In some embodiments, multiple medicated chews are administered to a subject at the same time, e.g., within 1 hour, within 30 minutes, or within 10 minutes. In some embodiments, the total amount of sennoside administered in a 24 hour period to a subject does not exceed 35 mg. In some embodiments, the medicated chew can be given once per day or multiple times per day in the form of divided doses, such as twice, thrice or four times a day, or at bedtime, as needed or as directed by a physician. In some embodiments, the serving size of the present disclosure is 2 medicated chews per serving, with each chewable medicated composition containing not less than about 4.3 mg sennoside.

The chewable medicated compositions described herein do not require gelatin as the gelling agent. The compositions are also substantially free of gluten. The present disclosure provides a plant-based gelling agent that can fully replace animal-derived products like gelatin, such that the final product is suitable not only for vegetarians, vegans and religious groups, but also for those suffering (even without knowing) from a celiac disease. Furthermore, the disclosure provides a natural gelling agent with reliable availability, and one that is economically viable. In particular, the chewable medicated compositions of the present disclosure are aimed at providing gelatin-free and gluten-free chewable compositions that display elasticity, texture profile and mouthfeel comparable or better than that of the standard gelatin based gummies, while being substantially sugar-free.

In some embodiments, the chewable medicated compositions described are gelatin-free, substantially free of gluten, and substantially free of sugar. In some embodiments, the chewable medicated compositions described are gelatin-free, gluten-free, and substantially free of sugar. In some embodiments, the chewable medicated compositions described are gelatin-free, gluten-free, and sugar-free. The term "substantially free" as used herein with regards to sugar means each sennoside chewable medicated composition contains less than 0.5 grams of sugar, both natural and added.

The term "substantially free" as used herein with regards to gelatin and gluten refers to a composition that has less than 1% wt/wt, less than 0.1% wt/wt, or less than 0.01% wt/wt of the substance in the composition. In some embodiments, the term gelatin-free and gluten-free indicates that the composition comprises an undetectable amount of the substance in the composition.

The term "a sennoside" refers to one or more compounds from a senna extract, e.g., a compound as presented as below—

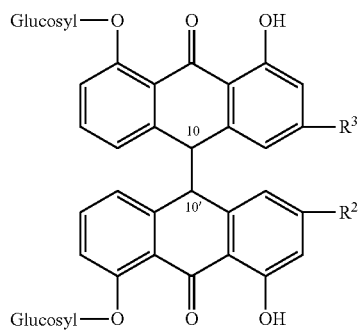

In some embodiments, $R^1$ can be COOH, CH$_2$OH, CH$_2$COOH, or CH$_2$CH$_2$COOH. In some embodiments, $R^1$ can be COOH or CH$_2$OH. In some embodiments, $R^2$ can be COOH or CH$_2$COOH or CH$_2$CH$_2$COOH. In some embodiments, 10-10' can be Trans or Meso. In some embodiments, the term "a sennoside" can be one or more of Sennoside A, Sennoside B, Sennoside C or Sennoside D as described below:

| R1 | R2 | 10-10' | Glycoside |
|---|---|---|---|
| COOH | COOH | Trans | Sennoside A |
| COOH | COOH | Meso | Sennoside B |
| CH2OH | COOH | Trans | Sennoside C |
| CH2OH | COOH | Meso | Sennoside D |

For clarity, the term "a sennoside" can include a single type of sennoside, e.g., Sennoside A, or a mixture of two or more sennosides, e.g., Sennoside A and Sennoside B. In some embodiments, the term "a sennoside" can include a mixture Sennoside A, Sennoside B, Sennoside C and Sennoside D.

The chewable medicated compositions of the present disclosure can comprise sennosides as the active ingredient, and one or more excipients selected from gelling agents, sweetening agents, pH adjusting agents, dietary fibres, flavouring agents and a coloring agent.

The chewable medicated compositions may optionally include additional ingredient, such as prune extract.

In some embodiments, the medicated chew comprises an effective amount of sennoside, e.g., in the range of about 0.05% w/w to about 5% w/w of the total composition, about 0.1% to about 2% of the composition, or about 0.5% to about 2% of the composition, such that each medicated chew contains not less than about 4.3 mg of sennosides. In some embodiments, the sennoside is about 0.05% w/w to about 2.5% w/w, about 0.05% w/w to about 2% w/w, about 0.05% w/w to about 1.5% w/w, 0.05% w/w to about 1% w/w, about 0.9% w/w, about 0.8% w/w, about 0.7% w/w, about 0.6% w/w, about 0.5% w/w, about 0.4% w/w, about 0.3% w/w, about 0.2% w/w or about 0.1% w/w of the total composition. Typically, the sennosides are used in the form of a leaf extract, as a dried powder or liquid extract, that may have a strength of from about 10% to about 70%.

In some embodiments, gelling agents are gel-forming agents which dissolve in a liquid phase to form a colloidal mixture that forms a weakly cohesive internal structure in a composition. In some embodiments, a gelling agent can include an organic hydrocolloid or hydrophilic inorganic substance. Suitable gelling agents include, but are not limited to, carrageenan, pectin and combinations thereof.

Examples of carrageenan that may be used may include kappa (k) carrageenans, Iota carrageenan and lambda (l) carrageenan. In one embodiment, the carrageenan used is a free flowing powder having a gel strength ranging between 400 to 1300 g/cm$^2$ (when measured for a 1.5% solution in IPA with a 1 cm$^2$ probe), moisture content of not more than 12%, pH ranging between 7 to 12, particle size such that not less than 80% particles pass through USS#100 mesh, and has aerobic plate count of less than 1000 cfu/g and total coliforms less than 500 cfu/g. In another embodiment, the carrageenan used is a free-flowing powder having a gel strength ≥800 g/cm$^2$ (when measured for a 1.5% solution in IPA with a 1 cm$^2$ probe), moisture content of not more than 12%, pH ranging between 7 to 10, particle size such that ≥95% particles pass through USS#80 mesh, and has aerobic plate count of less than 5000 cfu/g and total coliforms less than 100 cfu/g.

Pectin is a purified carbohydrate product obtained from the dilute acid extract of the inner portion of the rind of citrus fruits or from apple pomace. It consists chiefly of partially methoxylated polygalacturonic acids. Pectins can include citrus pectin, methopectin, methyl pectin, methyl pectinate, mexpectin, pectina or pectinic acid. Pectin can be used as a gelling agent in the chewable medicated compositions of the present disclosure either alone or in combination with carrageenan. When the chewable medicated composition of the present disclosure includes a mixture of carrageenan and pectin as a gelling agent, the two agents are present in a ratio ranging from about 10:90 to about 90:10. In some embodiments, carrageenan and pectin are used in a ratio of about 90:10 to about 50:50, or about 90:10 to about 70:30. In some embodiments, carrageenan and pectin are used in a ratio of about 90:10. In still more embodiments, carrageenan and pectin are used in a ratio of about 80:20. In still more embodiments, carrageenan and pectin are used in a ratio of about 70:30 by total weight of the composition.

The gelling agent can be present in the range of about 0.1% w/w to about 10% w/w of the total composition. In some embodiments, the gelling agent is present in the range of about 0.1% w/w to about 9% w/w, about 0.1% w/w to about 8% w/w, about 0.1% w/w to about 7% w/w, about 0.1% w/w to about 6% w/w, about 0.1% w/w to about 5% w/w, about 0.1% w/w to about 4% w/w, about 0.1% w/w to about 3% w/w, about 0.1% w/w to about 2% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w or about 2% w/w of the total composition.

Sweeteners or sweetening agents that may be used in the chewable medicated compositions of the present disclosure include any compounds that provide a sweet taste. This includes nutritive sweetening agents, non-nutritive sweetening agents and mixtures thereof. The nutritive sweetening agents may be selected from, but are not limited to, agave nectar, brown rice syrup, hydrogenated glucose syrup, date sugar, honey, molasses and blackstrap molasses, sorghum syrup, stevia, maple syrup, birch syrup, yacon syrup, lucuma powder, coconut sugar, erythritol, maltitol, mannitol, sorbitol, xylitol, isomalt crystals, lactitol, maltitol and mixtures thereof. The non-nutritive sweetening agents may be selected from, but are not limited to, acesulfame, advantame, alitame, allulose, aspartame, neotame, saccharin, sodium saccharin, sucralose, acesulfame potassium, tagatose, thaumatin, stevioside and mixtures thereof.

The chewable medicated compositions contain sweetening agent in the range of about 10% w/w to about 90% w/w of the total composition. Typically, the sweetening agent is present in the range of about 10% w/w to about 85% w/w, about 10% w/w to about 80% w/w, about 10% w/w to about 75% w/w, or about 10% w/w to about 70% w/w of the total composition.

In some embodiments, the sennoside chewable medicated composition of the present disclosure is substantially sugar free, and may contain no added sugar. The term "substantially free" as used herein with regards to sugar means each sennoside chewable medicated composition contains less than 0.5 grams of sugar, both natural and added. In some embodiments, the term "substantially sugar free" means each sennoside chewable medicated composition contains less than 1% wt/wt, less than 0.1% wt/wt, or less than 0.01% wt/wt of sugar in the composition. The term "sugar" when used in a phrase such as "substantially free of sugar", "sugar-free," and "substantially sugar free" refers to naturally occurring mono- and di-saccharides, and does not include sugar alcohols or sugar derivatives such as isomaltol or isomalt crystals. Thus, the term sugar-free may include compositions comprising greater than 1% erythritol, maltitol, mannitol, sorbitol, xylitol, lactitol, isomaltol and isomalt crystals.

In some embodiments, the chewable medicated composition comprises a dietary fiber. In some embodiments, the dietary fiber comprises, but is not limited to, inulin, ginger, oligofructose, beta-glucans and the like and mixtures thereof. In some embodiments, the dietary fiber is in the range of about 0.5% w/w to about 20% w/w of the total composition. In some embodiments, a dietary fiber is present in the range of about 0.5% w/w to about 19% w/w, about 0.5% w/w to about 18% w/w, about 0.5% w/w to about 17% w/w, about 0.5% w/w to about 16% w/w, about 0.5% w/w to about 15% w/w, about 0.5% w/w to about 14% w/w, about 0.5% w/w to about 13% w/w, about 0.5% w/w to about 12% w/w, about 0.5% w/w to about 11% w/w, about 0.5% w/w to about 10% w/w, about 9%, about 8%, about 7%, about 6%, about 5%, about 4%, about 3%, about 2%, about 1% of the total composition.

Buffering agents can be used in the chewable medicated compositions of the present disclosure to maintain the pH of the sennoside containing composition. Non-limiting examples of buffering agents that may be used include citric acid, malic acid, succinic acid, fumaric acid, tartaric acid, phosphoric acid, boric acid and ascorbic acid, sodium citrate, sodium tartarate, sodium acetate, sodium carbonate, sodium polyphosphate, potassium polyphosphate, sodium pyrophosphate, potassium pyrophosphate, potassium citrate, tripotassium citrate, disodium hydrogen phosphate, dipotassium hydrogen phosphate, trisodium phosphate, trisodium citrate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts and pharmaceutically acceptable salts thereof. In some embodiments, the buffer in the sennoside chewable medicated composition described herein comprises trisodium citrate. In another embodiment, the buffer comprises tripotassium phosphate. In yet another embodiment, tripotassium citrate is used as the buffer. In some embodiments, the buffer used is trisodium phosphate.

The buffering agent(s) can be present in an amount such that the chewable medicated composition of the present disclosure containing sennoside as the active ingredient is maintained within a range of about 3 to about 6. In some embodiments, the chewable medicated compositions of the present disclosure containing sennosides have a pH of about 4.5.

Sennoside being bitter, based on the formation mechanism of bitter taste, a commonly used masking approach is adding sweet taste substances, flavors, and/or effervescent agents to interfere with the perception of the bitter drug.

A flavoring agent or flavorant can be added to enhance the taste or aroma of the chewable medicated composition of the disclosure. Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, mango, grape, grapefruit, guava, hop, lemon, licorice, lime, elderberry, malt, mandarin, molasses, nutmeg, mixed berry, orange, peach, pear, peppermint, pomegranate, pineapple, raspberry, rose, spearmint, strawberry, tangerine, tea, vanilla, winter green, and the like, as well as combinations thereof. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular, wild cherry), grape, bubblegum, vanilla, and mixed berry. In one embodiment, the sennoside chewable medicated composition described herein comprises a mango flavor. In another embodiment, the sennoside chewable medicated composition comprises a ginger flavor. In another embodiment, the sennoside chewable medicated composition comprises a pomegranate flavor. In yet another embodiment, the sennoside chewable medicated composition comprises a grape flavor. In yet another embodiment, the sennoside chewable medicated composition comprises an elderberry flavor. In yet another embodiment, the sennoside chewable medicated composition comprises a cherry flavor.

The sennoside chewable medicated compositions may also comprise a coloring agent for identity and/or aesthetic purposes. Suitable coloring agents include natural colors as well as synthetic colors, such as FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide and mixtures thereof. The coloring agent may be present in an amount ranging from about 0.01% w/w to about 2.5% w/w of the total composition.

Water activity in a medicated chew or gummy is critical and impacts texture, deliquescence, phase transitions, moisture movement between components and more. It is more precise than moisture content measurement—roughly about 15 times more precise. The definition of water activity is 'the ratio of partial pressure of water above a product to that of pure water at the same temperature.' Pure water has a water activity of 1.00 aw, while the range of water activities goes from 0 to 1.00 for excipients used. The present disclosure provides that moisture plays a key role in the texture and taste of the sennoside medicated chews. Low moisture led to rock-hard adhesive-like product that can stick jaws, and high moisture can result in a sticky product. Further, moisture content, if not right, was found to lead to moisture migration during storage and affect the shelf life of the product. Therefore, controlling the moisture or water activity of the medicated chews of the present disclosure was very important. In some embodiments, the sennoside medicated chew of the present disclosure has a water activity in the range of about 0.6 aw to about 0.85 aw, or about 0.65 aw to about 0.8 aw. In some embodiments, the sennoside medicated chew of the present disclosure has a water activity of about 0.7 aw. The water activity of the medicated chews of the present disclosure may be measured by methods conventional in the art and known to skilled persons.

The sennoside chewable medicated compositions of the present disclosure may be coated with wax to reduce stickiness of the formulation. Wax may be plant or animal-based wax, selected from, but not limited to, organic sunflower seed wax, carnauba wax, soy wax, rice bran wax, candelilla wax, beeswax, and the like and combinations thereof. In some embodiments of the disclosure, the sennoside chewable medicated composition is coated with sunflower seed wax. Typically, the seed wax is applied on the moulds before the product is deposited on them, and/or may also be used to polish the finished chewable medicated composition. This also helps to obtain compositions that are non-sticky.

The sennoside chewable medicated compositions described herein are stable under various storage conditions, including refrigerated, ambient and accelerated conditions. Stable, as used herein, can refer to chewable medicated composition comprising sennoside as the active agent characterized in that the total microbial count remains <1500 CFU/g when stored for at least 18 months, preferably for at least 24 months, at ambient temperature with minimum exposure to sunlight. In some embodiments, stable can refer to the physical integrity of the product, e.g., it maintains its water activity for at least 12 months, at least 18 months or at least 24 months. In some embodiments, stable can refer to the chemical stability of the sennoside, i.e., the sennoside does not degrade. In some embodiments, the medicated chew has chemical stability for at least 12 months, at least 18 months or at least 24 months.

At ambient temperature with minimum exposure to sunlight, the stable sennoside chewable medicated compositions of the present disclosure are stable for at least 12 months, 24 months or 36 months. The term "shelf life" refers to the amount of time the chewable medicated composition may be stored without loss of potency and/or performance profile. In some embodiments of the present disclosure, shelf life refers to the amount of time the chewable medicated composition may be stored without loss of 2%, 5%, 8% or 10% of the potency and/or performance. Further, the sennoside medicated chews of the present disclosure have a high melting point, such that the chews are not impacted by high temperatures that may be faced during transport and storage. Typically, the sennoside medicated chews of the present disclosure have a melting point in the range of about 70° C. to about 90° C., more preferably about 80° C. to about 85° C.

In some embodiments, the disclosure provides for a process for making the medicated chews provided herein. In some embodiments, the process of making sennoside chewable medicated composition of the present disclosure involves the following stages—

Stage 1: Gel melting a. Take suitable quantity of water into a cooker and heat it to boiling point (about 100° C. to about 125° C.).

b. Add gelling agent to step (a) and stir for about 10 to about 15 minutes to get a clear solution.

c. Add sweetener to step (b) as soon as gelling agent is dissolved (within about 15 to about 60 minutes) and maintain the temperature between about 80° C. to about 120° C.

Stage 2: Active blending d. Add suitable quantity of the senna extract, one or more flavouring agent, one or more dietary fiber and stir for about 10 to about 15 minutes to get a clear solution. Continue boiling until the solids in the solution reach 65-70 brix as measured by brix spindle.

e. Optionally add another sweetening agent to step (d) and mix well until it completely dissolves.

f. Add suitable buffering agent to step (e) at a temperature of about 70° C. to about 90° C. and mix well for about 10 to about 30 minutes. If required, add pH adjusting agent to adjust the pH to the desired pH of about 4.5.

g. Cook product mass of step (f) until about 65% to about 70% of brix is reached. Heat the mass to a suitable temperature in the range of about 70° C. to about 95° C.

Stage 3: Excipient blending h. Excipient blending: At 90° C. add edible essence, edible colorant and the other remaining ingredients to step (g), and homogenously stir and blend the mixture further. Measure the viscosity and specific gravity to ensure it is within the desired range.

Stage 4: Casting moulding i. Perform casting by transferring the blended solution of step (h) to a casting machine.

Stage 5: Drying j. Transfer the gummy candy product obtained after casting moulding in step (i) to a confined space at about 20° C. to about 35° C. and a relative humidity of about 15% to about 40%, and drying the product to a water content of about 10% to about 25%.

k. Subject the dried product to demoulding, polishing and packaging to obtain the final product.

The process for making the sennoside chewable medicated compositions of the present disclosure as described herein is suitable in obtaining the product with desired properties, such as content uniformity, non-sticky texture and stability. Sennosides being potent and required in a very low quantity, it is important to ensure content uniformity of the chewable medicated composition. In some embodiments, the order of addition, the rate of addition and the pH at which the senna extract is added to the candy mass can be important. In some embodiments, if not followed as described herein, lumps can form and the sennosides may get non-uniformly distributed in the mass, impacting content uniformity of the medicated chew. The total quantity of the sennosides may be added to the candy mass in a single lot, or may be added in divided lots over a period of time. Typically, the amount of senna extract may include about 0.05% w/w to about 20% w/w overages to compensate for any losses during manufacture and storage.

The sennoside chewable medicated compositions of the present disclosure may be packaged in inert HDPE bottles with child resistant caps (CRC) of suitable size. In some embodiments, the medicated chews may be packaged in child-resistant blister packs. In some embodiments, the blister packs can assist in controlling doses or indicating serving sizes for subjects. Blister packs can also help control a subject's product usage, by assisting subjects to know how much of a product they should use or take. The packaging may contain desiccants to prevent deleterious effects of moisture on the chewable medicated compositions. The use of blister packaging may also control excessive consumption of the gummies.

The packaged sennoside chewable medicated compositions possess a content uniformity that meets the requirements of the USP<905>Uniformity of Dosage Units test. The term "uniformity of dosage unit" is defined as the degree of uniformity in the amount of the drug substance among dosage units. The test for "Content Uniformity" of compositions presented in dosage units is based on the assay of the individual content of drug substance(s) in a number of dosage units to determine whether the individual content is within the limits set. The content uniformity is defined by an acceptance value of <15.0, preferably ≤10.0, more preferably <7.5. The "acceptance value" can be determined according to Ph. Eur. 2.9.40/ USP<905>. The test is typically carried out by weighing an equal number of units individually to obtain a total of not less than 20 individual weights, and the average weight is calculated. The requirements are met if no individual weight differs from the average weight by more than 7.5%. If 1 unit falls outside of the limits, the procedure is repeated with an additional set of not less than 20 chewable gels. The requirements are met if none of the units tested differ from the average weight by more than 10%.

In some embodiments, the assay of sennosides in the packaged sennoside chewable medicated composition is in the range of about 85% to about 115% (by weight) of the product label claim as determined by USP method for the finished product, and/or as compared to other sennoside containing dosage forms that may be available on the market.

The rate of disintegration of the compositions of the present disclosure can be measured using various in vitro test methods, for example the USP<701>Disintegration Test.

Definitions

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the invention.

Unless the context indicates otherwise, it is specifically intended that the various features of the disclosure described herein can be used in any combination.

Moreover, the present disclosure also contemplates that in some embodiments of the disclosure, any feature or combination of features set forth herein can be excluded or omitted.

All publications, patent applications, patents, and other references mentioned herein are incorporated by reference herein in their entirety for all purposes.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this disclosure, dose, time, temperature, and the like, is meant to encompass variations of ±20% of the specified amount.

The terms "senna", "senna extract", "sennoside", "sennosides" may be used interchangeably.

The term "non-sticky" means having a firm, dry, and brittle surface or texture.

The term "stable" as used herein refers to physical and chemical stability of sennoside chewable medicated composition.

The term "substantially gluten free" can mean total gluten content of the formulation is <20 ppm.

The term "chewable medicated composition" may be used interchangeably with medicated chew, gummies, gummy bears, gum drops, jelly candy, gummi chews, chewable gels, chew gels, gummy candy, gummies, jelly fruit candy, confectionery or jellies. The present disclosure is further illustrated by reference to the following examples which are for illustrative purpose only and do not limit the scope of the disclosure in any manner.

Example 1

| Ingredients | Quantity (% w/w) |
| --- | --- |
| Senna extract | 0.63 |
| Maltitol Syrup | 35.23 |
| Isomaltose Oligosaccharides | 34.00 |
| Purified water | 25.54 |
| Carrageenan | 1.30 |
| Citric acid (anhydrous) | 0.26 |
| Trisodium citrate | 0.28 |
| Cherry Flavor | 1.02 |
| Inulin | 0.44 |
| Liquorice | 0.15 |
| Elderberry extract | 0.38 |
| Organic pomegranate | 0.28 |
| Organic ginger | 0.28 |

The medicated chew was obtained by the following manufacturing process. A suitable quantity of water was taken into a cooker and heated to boiling point. Carrageenan was then added with stirring, and stirring was continued for about 10 to about 15 minutes to get a clear solution. Warm lycasin syrup was added to this as soon as carrageenan is dissolved (within about 5 to about 30 minutes) while maintaining the temperature between about 100° C. to about 120° C. A suitable quantity of senna extract, elderberry extract, organic pomegranate, organic ginger was then added to the solution and stirred for about 10 to about 15 minutes to get a clear solution. The boiling was continued until the solids in the solution reached 65-70 brix as measured by brix spindle. Isomalt Crystals were then added and mixed well until they completely dissolved. This was followed by additions of trisodium citrate to the solution at a temperature of about 70° C. to about 90° C., and was further followed by mixing well for about 15 to about 30 minutes. The pH was checked at this stage. If required add citric acid was added to adjust the pH to the desired pH of about 4.5 . The product mass was cooked until about 65% to about 70% of brix was reached. The mass was heated to a suitable temperature, and at about 90° C. inulin, cherry flavour and licorice masking agent was added. The mass was homogenously stirred and blended. The viscosity and specific gravity of the mass was measured at this stage.

The blended solution was transferred to a casting machine to obtain the gummies. These were then dried at about 20° C. to about 30° C., at a relative humidity of about 15% to about 40%, until the water content of the product was about 10% to about 25%. Finally, the dried product was subjected to demolding, polishing and packaging in blisters. The medicated chew thus obtained has a water activity of 0.7058 aw and a melting point of 83.6° C.

Example 2

| Ingredients | Quantity (% w/w) |
| --- | --- |
| Senna extract | 0.64 |
| Sorbitol | 35.81 |
| Isomaltose Oligosaccharides | 34.61 |
| Purified water | 26.02 |
| Pectin | 0.13 |
| Carrageenan | 1.19 |
| Trisodium citrate | 0.29 |
| Citric acid anhydrous | 0.27 |
| Flavor | 1.04 |

The medicated chew of Example 2 containing pectin and carrageenan was obtained by following a manufacturing process similar to that of Example 1 above.

The invention claimed is:

1. A medicated chew comprising a sennoside, about 0.1% w/w to about 10% w/w of a gelling agent selected from the group consisting of carrageenan, pectin or mixtures thereof, about 10% w/w to about 90% w/w of a sweetening agent, and a buffer, wherein the pH of the medicated chew is about 3 to about 6, and wherein the medicated chew is substantially free of sugar, gelatin and gluten, wherein the medicated chew is a gummy, gummy bear, gum drop, jelly candy, gummy chew, chewable gel, chew gel, gummy candy, jelly fruit candy, confectionery, or jelly.

2. The medicated chew of claim 1, wherein the medicated chew has a water activity of about 0.6 aw to about 0.85 aw.

3. The medicated chew of claim 1, wherein the sennoside is about 0.05% w/w to about 2.5% w/w of the medicated chew.

4. The medicated chew of claim 3, wherein the medicated chew comprises not less than about 4.3 mg sennoside.

5. The medicated chew of claim 1, wherein the gelling agent is carrageenan.

6. The medicated chew of claim 5, wherein the carrageenan is about 1.2% w/w to about 1.5% w/w of the medicated chew.

7. The medicated chew of claim 1, wherein the gelling agent is a mixture of carrageenan and pectin.

8. The medicated chew of claim 7, wherein the mixture of carrageenan and pectin is about 1.2% w/w to about 1.5% w/w of the medicated chew.

9. The medicated chew of claim 1, wherein the buffer comprises citric acid, malic acid, succinic acid, fumaric acid, tartaric acid, phosphoric acid, boric acid and ascorbic acid, sodium citrate, sodium tartarate, sodium acetate, sodium carbonate, sodium polyphosphate, potassium polyphosphate, sodium pyrophosphate, potassium pyrophosphate, potassium citrate, tripotassium citrate, disodium hydrogen phosphate, dipotassium hydrogen phosphate, trisodium phosphate, trisodium citrate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and mixtures thereof.

10. The medicated chew of claim 9, wherein the buffer is a mixture of citric acid and trisodium citrate.

11. The medicated chew of claim 1, wherein the medicated chew is stable for at least 24 months.

* * * * *